United States Patent
Dev et al.

(10) Patent No.: US 10,765,109 B1
(45) Date of Patent: Sep. 8, 2020

(54) DIELECTRIC DETECTOR FOR PEST INFESTATIONS

(71) Applicant: Florida A&M University, Tallahassee, FL (US)

(72) Inventors: Satyanarayan Dev, Tallahassee, FL (US); Benjamin Hottel, Tallahassee, FL (US); Aavudai Anandhi Swamy, Tallahassee, FL (US)

(73) Assignee: Florida A&M University, Tallahassee, FL (US)

( * ) Notice: Subject to any disclaimer, the term of this patent is extended or adjusted under 35 U.S.C. 154(b) by 151 days.

(21) Appl. No.: 16/148,580

(22) Filed: Oct. 1, 2018

Related U.S. Application Data (60) Provisional application No. 62/565,772, filed on Sep. 29, 2017.

(51) Int. Cl.
| | | |
|---|---|---|
| *A01M 99/00* | (2006.01) | |
| *A01G 7/06* | (2006.01) | |
| *G01N 27/24* | (2006.01) | |
| *G01N 27/22* | (2006.01) | |
| *G01N 22/02* | (2006.01) | |

(52) U.S. Cl.
CPC ............... *A01M 99/00* (2013.01); *A01G 7/06* (2013.01); *G01N 22/02* (2013.01); *G01N 27/221* (2013.01); *G01N 27/24* (2013.01)

(58) Field of Classification Search
CPC .......... A01M 99/00; A01G 7/00; A01G 7/06; G01N 22/00; G01N 22/02; G01N 27/00; G01N 27/02; G01N 27/22; G01N 27/221; G01N 27/24

USPC ....... 324/600, 629, 637, 642, 649, 658, 663, 324/500, 512, 527, 532, 533, 534
See application file for complete search history.

(56) References Cited

U.S. PATENT DOCUMENTS

| | | | |
|---|---|---|---|
| 5,285,688 A * | 2/1994 | Robbins | A01M 1/026 73/587 |
| 5,896,696 A | 4/1999 | Stokes et al. | |
| 6,404,210 B1 * | 6/2002 | Su | A01M 1/026 324/692 |
| 6,937,156 B2 | 8/2005 | Gardner, Jr. et al. | |
| 7,994,800 B2 * | 8/2011 | Andarawis | H03D 13/00 324/601 |
| 9,880,146 B2 * | 1/2018 | Troxler | G01N 23/02 |
| 2003/0178034 A1 * | 9/2003 | Yuki | G01S 13/887 340/568.1 |
| 2005/0212529 A1 * | 9/2005 | Huang | G01Q 60/40 324/633 |
| 2014/0049274 A1 * | 2/2014 | Hafer | G01F 23/0061 324/681 |
| 2016/0143558 A1 * | 5/2016 | Chernokalov | G01S 13/88 600/430 |
| 2019/0104715 A1 * | 4/2019 | Ben Hamozeg | G08C 17/02 |

FOREIGN PATENT DOCUMENTS

EP          0283142 A1    9/1988

* cited by examiner

*Primary Examiner* — Hoai-An D. Nguyen
(74) *Attorney, Agent, or Firm* — Smith & Hopen, P.A.; Steven M. Forte (57) ABSTRACT

Methods and systems for detecting pests, such as termites, in living organisms, such as trees. Certain embodiments of the current invention utilize time domain reflectometry to detect the pests. Other embodiments of the current invention utilize microwave-coupled transmission spectrometry antenna array transmitters, and receivers to detect the pests.

15 Claims, 4 Drawing Sheets

DIELECTRIC DETECTOR FOR PEST INFESTATIONS

CROSS-REFERENCE TO RELATED APPLICATION

This nonprovisional application claims priority to U.S. Provisional Patent Application No. 62/565,772, entitled "Dielectric Detector for Pest Infestations," filed Sep. 29, 2017 by the same inventors, the entirety of which is incorporated herein by this reference.

TECHNICAL FIELD

This invention relates, generally, to pest control. More specifically, it relates to pest detection within living organisms.

BACKGROUND

Termites are wood feeding insects that live in large social colonies, similar to honeybees and ants. In forests, termite colonies play an important role in nature by feeding on decaying wood found on the soil floor. Formosan termites are also different from native species in that they will infest living trees at a higher rate than their native counterparts. Many species of trees ranging from pine to live oak trees have been infested with this species of termites.

Formosan termites feed on the hardwood, the dead center of a tree, and can end up leaving the tree hollow. After hollowing out the tree, the termites will fill in the hollowed-out area with nesting material. The hollowed-out trees are more susceptible to falling from wind damage during heavy storms.

In New Orleans, La., 75% of trees that fall after hurricanes are found to have fallen due to Formosan termite-related damage. Considering that up to 100% of the trees in certain areas of New Orleans have been found to be infested with these termites, the structural integrity of many of these trees would be in question if a heavy storm were to pass through the city. Jacksonville, Fla. has recently discovered that many of the trees in the Riverside community area of Jacksonville have Formosan termite activity as well. Measures are being taken in Jacksonville to work with pest control companies to help manage these termite infestations on public property.

Additionally, there have been several reports of Formosan termites infesting living trees in Leon County. Many of the trees in the area are at risk, including the historic live oak trees found throughout the county. During Hurricane Hermine, many homeowners in Leon County experienced first-hand the damage that falling trees can cause. Since these termites can increase the likelihood that infested trees will fall over in a storm, the spread of these termites into the live tree fauna of Leon County could lead to increased property damage in any future heavy storm event. Attempts have been made to use capacitance sensors to detect and trap pests, such as U.S. Pat. No. 6,937,156 to Gardner, Jr. et al., however, no system has been devised to detect pests or damage from infestation in a living system.

With this significant problem, however, no effective solution exists for detecting pests within trees and other living systems. Accordingly, what is needed is a system and methodology for detecting and/or controlling pests in living systems, such as termites in trees in order to be better prepared for heavy storm events in the future. However, in view of the art considered as a whole at the time the present invention was made, it was not obvious to those of ordinary skill in the field of this invention how the shortcomings of the prior art could be overcome.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

SUMMARY

This summary is provided to introduce a selection of concepts in a simplified form. These concepts are described in further detail in the detailed description of example embodiments of the disclosure below. This summary is not intended to identify key features or essential features of the claimed subject matter, nor is it intended to be used to limit the scope of the claimed subject matter.

Embodiments disclosed herein include a system for detecting pests and the damage from infestation, including a plurality of capacitive electrode sensors; a plurality of transmission lines; a capacitive sensing time domain reflectometry (TDR) device, wherein the TDR device is both a source and detector of signals transmitted to and from a region of detection or area of interest; a probe configured to enclose the plurality of transmission lines, wherein the distal end of the probe is configured to be operably linked to the plurality of capacitive electrode sensors; wherein a signal is transmitted from the TDR device as an incident waveform along the plurality of transmission lines to the capacitive electrode sensors; the signal is then reflected from the capacitive electrode sensors back along the plurality of the transmission lines to the TDR device; wherein the TDR device is operably linked to a mobile device which displays the results from the capacitance electrode sensors.

In additional embodiments, the system for detecting pests and damage from infestation wherein the probe is configured to penetrate a living tree. The system for detecting pests and damage from infestation, wherein the capacitance electrode sensors are configured to collect data on pest activity or damage from pest infestation. The system for detecting pests and damage from infestation, wherein the mobile device is a computer operably linked to a printer to print out the results from the capacitance electrode sensors. The system for detecting pests and damage from infestation, wherein the mobile device further comprises a display which is configured to display the results from the capacitance electrode sensors.

The system for detecting pests and damage from infestation, wherein the pest consists of termites or emerald ash borers. The system for detecting pests and damage from infestation, wherein the damage from infestation results in a loss of wood from inside a living tree leaving the tree to some degree hollow.

The system for detecting pests and damage from infestation, wherein the living tree consists of a pine, ash, or oak tree. The system for detecting pests and damage from infestation, wherein the TDR is wirelessly linked to the mobile device.

In further embodiments, a system for detecting pests and the damage from infestation, the system including a microwave coupled transmitter, transmission spectrometry antenna (TSA) array, and receiver device, wherein the microwave device is both a source and detector of signals transmitted to and from a region of detection or area of interest; a microwave spectrum analyzer; a probe configured to improve penetration of microwave signal to the area of interest; wherein the microwave spectrum analyzer is tuned with the microwave TSA arrays and receiver to analyze the returning signal from the area of interest; wherein the microwave spectrum analyzer is operably linked to a mobile device which displays the results.

In additional embodiments, a method of detecting pests within a living system, the method includes providing a transmission line with a time domain reflectometry source/detector at a proximal end of the transmission line and a capacitance sensor at a distal end of the transmission line; inserting the capacitance sensor into an interior of the living system; generating a signal from the time domain reflectometry source/detector; transmitting an incident waveform of the signal distally along the transmission line and through the capacitance sensor into the interior of the living system; the capacitance sensor detecting and receiving the signal reflected from within the interior of the living system; transmitting a reflected waveform of the signal proximally along the transmission line until received by the time domain reflectometry source/detector; and processing the reflected signal to determine presence of the pests within the living system.

BRIEF DESCRIPTION OF THE DRAWINGS

For a fuller understanding of the invention, reference should be made to the following detailed description, taken in connection with the accompanying drawings, in which.

DETAILED DESCRIPTION

In the following detailed description, reference is made to the accompanying drawings, which form a part thereof, and within which are shown by way of illustration specific embodiments by which the invention may be practiced. It is to be understood that other embodiments may be utilized, and structural changes may be made without departing from the scope of the present application. These embodiments are described in sufficient detail to enable those of ordinary skill in the art to practice the present disclosure, and it is to be understood that other embodiments may be utilized, and that structural, logical, and electrical changes may be made within the scope of the disclosure.

From the following descriptions, it should be understood that components of the embodiments as generally described and illustrated in the figures herein could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

The following description provides specific details, such as material types, compositions, material thicknesses, and processing conditions in order to provide a thorough description of embodiments of the disclosure. However, a person of ordinary skill in the art will understand that the embodiments of the disclosure may be practiced without employing these specific details. Indeed, the embodiments of the disclosure may be practiced in conjunction with conventional techniques employed in the industry. Only those process acts and structures necessary to understand the embodiments of the disclosure are described in detail below. A person of ordinary skill in the art will understand that some process components are inherently disclosed herein and that adding various conventional process components and acts would be in accord with the disclosure. In this description, specific implementations are shown and described only as examples and should not be construed as the only way to implement the present disclosure unless specified otherwise herein.

Illustrations presented herein are not meant to be actual views of any particular material, component, or system, but are merely idealized representations that are employed to describe embodiments of the disclosure. Referring in general to the following description and accompanying drawings, various embodiments of the present disclosure are illustrated to show its structure and method of operation. Common elements of the illustrated embodiments may be designated with similar reference numerals. It should be understood that the figures presented are not meant to be illustrative of actual views of any particular portion of the actual structure or method but are merely idealized representations employed to more clearly and fully depict the present invention defined by the claims below.

It should be understood that any reference to an element herein using a designation such as "first," "second," and so forth does not limit the quantity or order of those elements, unless such limitation is explicitly stated. Rather, these designations may be used herein as a convenient method of distinguishing between two or more elements or instances of an element. Thus, a reference to first and second elements does not mean that only two elements may be employed there or that the first element must precede the second element in some manner. Also, unless stated otherwise a set of elements may comprise one or more elements.

Any headings used herein should not be considered to limit the scope of embodiments of the invention as defined by the claims below and their legal equivalents. Concepts described in any specific heading are generally applicable in other sections throughout the entire specification.

As used in this specification and the appended claims, the singular forms "a", "an", and "the" include plural referents unless the content clearly dictates otherwise. As used in this specification and the appended claims, the term "or" is generally employed in its sense including "and/or" unless the context clearly dictates otherwise.

As used herein, "about" means approximately or nearly and in the context of a numerical value or range set forth means±15% of the numerical. In an embodiment, the term "about" can include traditional rounding according to significant figures of the numerical value. In addition, the phrase "about 'x' to 'y'" includes "about 'x' to about 'y'".

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range.

The phrases "connected to" and "coupled to" refer to any form of interaction between two or more entities, including mechanical, electrical, magnetic, electromagnetic, fluid, and thermal interaction. Two components may be connected or coupled to each other even though they are not in direct contact with each other. For example, two components may be coupled to each other through an intermediate component.

The directional terms "proximal" and "distal" are used herein to refer to opposite locations on a medical device. The proximal end of the device is defined as the end of the device closest to the practitioner when the device is in use by the practitioner. The distal end is the end opposite the proximal end, along the longitudinal direction of the device, or the end furthest from the practitioner.

Referring in general to the following description and accompanying drawings, various embodiments of the present disclosure are illustrated to show its structure and method of operation. Common elements of the illustrated embodiments may be designated with similar reference numerals. Accordingly, the relevant descriptions of such features apply equally to the features and related components among all the drawings. Any suitable combination of the features, and variations of the same, described with components illustrated in FIG. 1, can be employed with the components of FIG. 2, and vice versa. This pattern of disclosure applies equally to further embodiments depicted in subsequent figures and described hereinafter. It should be understood that the figures presented are not meant to be illustrative of actual views of any particular portion of the actual structure or method but are merely idealized representations employed to more clearly and fully depict the present invention defined by the claims below.

All referenced publications are incorporated herein by reference in their entirety.

Furthermore, where a definition or use of a term in a reference, which is incorporated by reference herein, is inconsistent or contrary to the definition of that term provided herein, the definition of that term provided herein applies and the definition of that term in the reference does not apply.

Figure 1:
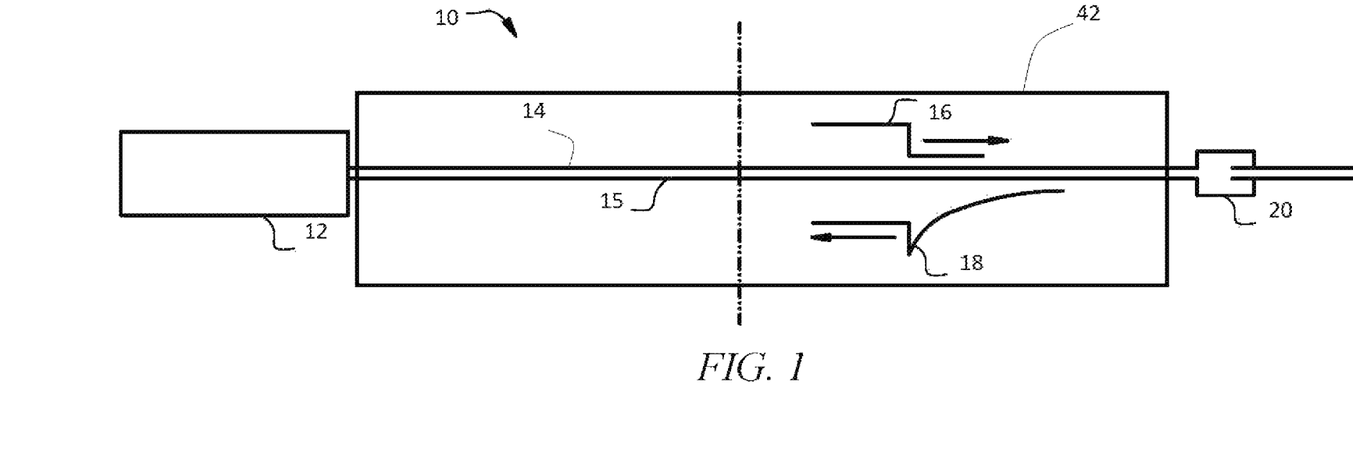
FIG. 1 is a schematic depicting an embodiment of the claimed subject matter.
Figure 2:
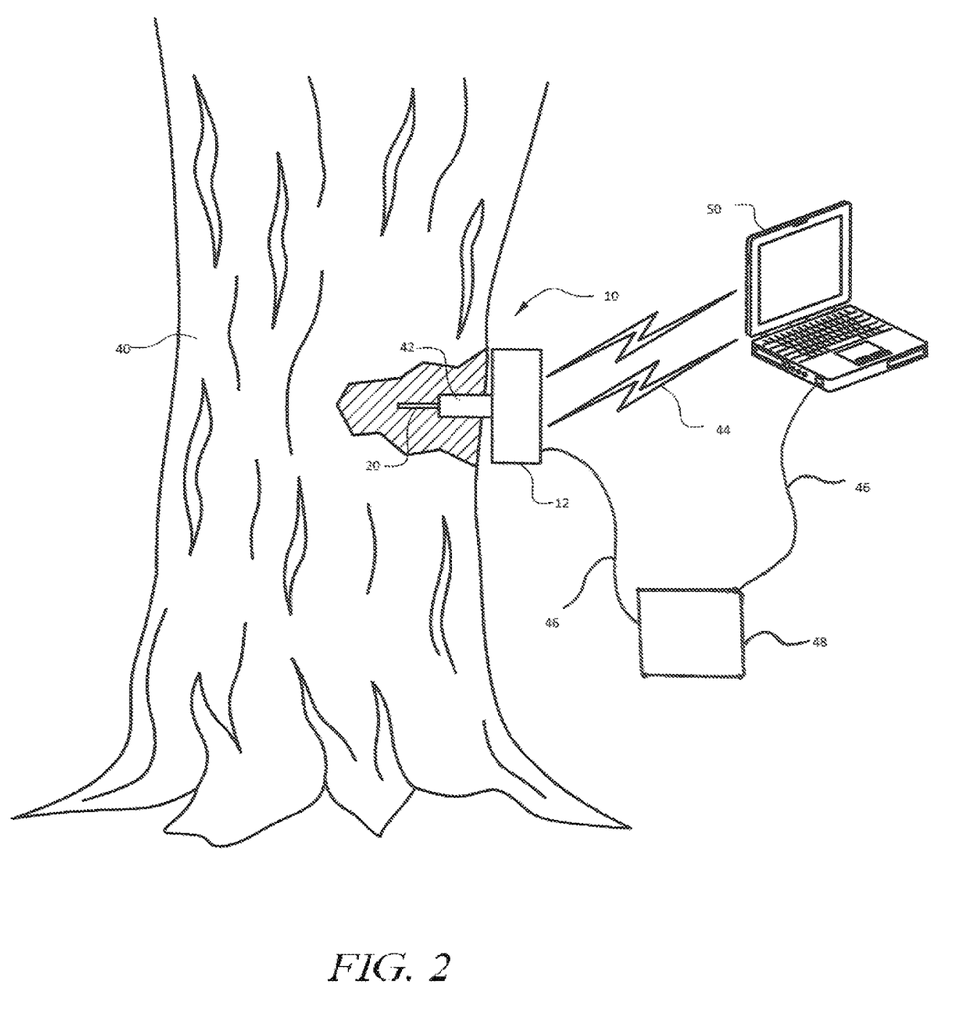
FIG. 2 depicts an alternative embodiment of the claimed subject matter in use on a living tree.

An embodiment of an apparatus 10 for detecting pest activity is depicted in FIG. 1. In an embodiment, apparatus 10 includes a detector means, such as capacitance sensor 20, which has a detection field in which a pest may be detected. When a non-capacitive object, such as a pest, approaches the capacitance sensor 20, capacitance sensor 20 can detect the presence of the pest because the body of the pest has a higher dielectric constant than air. In the embodiment depicted in FIG. 1, apparatus 10 uses time domain reflectometry (TDR). The time domain reflectometer 12 is both a source and a detector of signals transmitted to and from a region of detection. The apparatus 10 further includes a hollow probe 42 formed of an outgoing transmission line 14 and incoming transmission line 15 and a capacitance sensor 20 at a distal end of the transmission line 14. A signal is transmitted from the time domain reflectometer 12. An incident waveform 16 travels along outgoing transmission line 14 to the capacitance sensor 20 within the tree 40 (as depicted in FIG. 2 discussed below). When the signal is reflected, the reflected waveform 18 and corresponding signal are detected by the capacitance sensor 20. The reflected waveform 18 travels along incoming transmission line 15 to the time domain reflectometer 12.

It can be understood that, if termites have degraded the interior of the tree 40, then there would be less reflectance/impedance of the transmitted signals. The capacitance of the damaged region will be lower than the capacitance of an undamaged region of the tree. In this manner, the presence of termites within tree 40 can be determined, and appropriate treatment action can be taken.

In an embodiment, apparatus 10 depicted in FIG. 1 for monitoring the activity of pests includes a plurality of capacitance sensors 20 arranged in a capacitance sensing circuit (not depicted). When a non-capacitive object, such as a pest, approaches the capacitance sensors 20, the capacitance of the sensor electrodes increases due to the body of the pest having a higher dielectric constant than air. In a similar fashion, the linked capacitance sensing circuit (not depicted) detects the increased capacitance and provides a wireless data transmission 44 (as depicted in FIG. 2 discussed below) that indicates that a pest has entered the area being monitored. The capacitance sensing circuit may also be arranged to determine the size and type of pest based on the detected deviation of the output signal with respect to a baseline capacitance value.

The apparatus depicted in FIG. 1 monitors the activity of pests by employing capacitance sensor 20 depicted in FIG. 1 to detect changes of capacitance signal within a target region of tree 40 as compared to a baseline capacitance value. The deviation from the baseline indicates previous pest activity in the target region. Pest activity, as used in the present application, may refer to pests currently living within the target region of a living system, such as tree 40, prior damage caused by the pests within the target region of tree 40, or both. The pests may include, but are not limited to, termites and emerald ash borers in pine, ash, and oak trees.

The activity of the pests may be determined without capturing the pests and by identifying the damage caused by the pests. Apparatus 10 may further include hardware, software, firmware, or a combination thereof for monitoring additional data associated with the detected pest activity. The additional data may include the number of detected events, the time and date, and other parameters such as temperature, light, and humidity of the ambient environment. In some embodiments, the apparatus 10 may indicate a plurality of pests and the resulting environmental change from the activity of the plurality of the pests.

In an embodiment depicted in FIG. 2, apparatus 10 is depicted in use on a tree 40, including time domain reflectometer 12 which can be used in combination with a probe 42 to penetrate a tree 40. Time domain reflectometer 12 is operably linked to a probe 42 capable of penetrating the bark and interior of a tree 40 as depicted. The probe 42 is inserted into the tree 40 and positioned within about (3) to about five (5) inches from the target region. The capacitance sensor 20 can then extend from time domain reflectometer 12 through the hollow probe 42 into the tree 40. Time domain reflectometer 12 is then operably linked either via wires 46 or wirelessly 44 to a computing device 50 which is either a stand-alone computer or mobile device that is capable of processing the capacitance data and displaying the results. The computing device 50 is also able to transmit the capacitance data transmitted from the time domain reflectometer 12 to a printer or display (not depicted). In some embodiments the pest activity is detected when the signal from the detector provides a positive signal, in other embodiments the pest activity is detected when the signal from the detector provides a negative signal. Whether the pest activity results in a positive signal or negative depends on the living system under investigation, the specific time in the life cycle of the pest, and the type of pest causing the damage. For example, pest activity may lead to increased numbers of pests in comparison to undamaged regions of tree 40 which would lead to a positive signal than an undamaged area.

Figure 4:
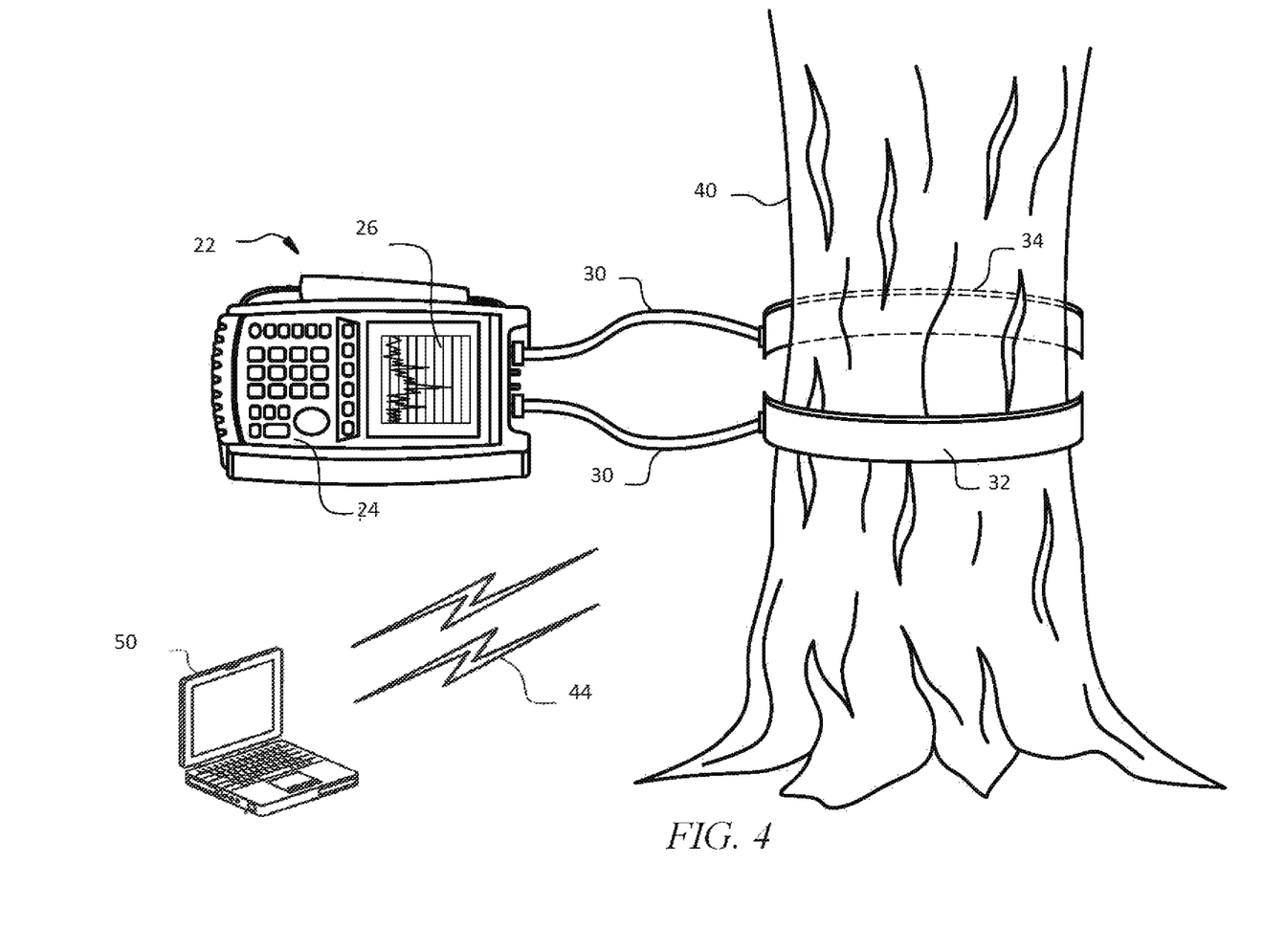
FIG. 4 depicts an alternative embodiment of the claimed subject matter in use on a living tree.

In an embodiment, apparatus 10 for monitoring the activity of pests includes a single time domain reflectometer 12, as depicted in FIG. 2. In an alternative embodiment of the claimed subject matter, the apparatus for monitoring the activity of pests includes a plurality of time domain reflectometers (not depicted) distributed over an area under surveillance, in communication with an indicator for reporting the presence or absence of a pest. In some circumstances, it would be difficult or undesirable to drill a probe 42 into the trunk of tree 40, in these circumstances the use of the portable dielectric detector 22 would not require drilling into the tree 40 (as depicted in FIG. 4).

Time domain reflectometer 12 depicted in FIG. 2 provides data on the changes in capacitance in tree 40 being monitored in comparison to a reference environment which indicates changes in the environment from pest activity. In some embodiments, a computing device 50 is operatively linked to time domain reflectometer 12 either wirelessly 44 or wired (not depicted), storing the signals for later analysis.

In an embodiment, capacitance sensor 20 is placed at the end of probe 42 depicted in FIG. 2. The hollow probe 42 penetrates tree 40 to allow the capacitance sensor 20 to take measurements inside tree 40. The probe 42 can be configured to penetrate into a target region to allow the capacitance sensor 20 to monitor for pest infestation or the damage from pest infestation. Time domain reflectometer 12 will transmit data indicating changes in capacitance in a target region to a relay 48. This transmission of data may take place over fixed wires 46 or wirelessly (not depicted).

The capacitance sensor 20 on the end of probe 42 may have various lengths depending on the type of pest or target region being monitored. In addition, the probe may be configured to reach varied target areas with curves in probe 42. The probe such as 42 depicted in FIG. 2, may be changeable so that the same device can be used to take readings from varied target regions, included within a tree 40 and trees with varying trunk size and bark thickness. The capacitance sensor 20 may be constructed separately out of copper foil or other conductive metal.

Apparatus 10 further includes relay 48. Relay 48 communicates capacitance value data from time domain reflectometer 12 to a computing device 50. This communication may take place over a fixed wire or wirelessly 44, such as depicted in FIG. 2. The computing device 50 may either be in a stand-alone computer or a mobile device running an application configured to display the sensor data and indicate the meaning of a change in capacitance. In an embodiment, RF based communication is used to connect time domain reflectometer 12 to the relay 48 as well as the computing device 50. In another embodiment, an IR-based communication is used to transmit data between time domain reflectometer 12 and the relay 48 and the computing device 50.

Time domain reflectometer 12 may include a memory device or other data storage to accumulate data which can then be communicated to a separate relay device 48 or computing device 50. Time domain reflectometer 12 may be constructed to archive pest presence or damage from past pest presence in an onboard memory location or in a separate memory device. The transmission of this stored data may be at set intervals, may be prompted by a user, or may be continuous.

Time domain reflectometer 12 provides data on the pest activity including the time and date of the reading, and any additional manually input data. One of skill in the relevant art will appreciate there are many methodologies that may be employed to transmit data from time domain reflectometer 12 to a relay 48 and a subsequent computing device 50 or mobile device equivalent to display the results.

Computing device 50 running an application may be special purpose devices or may be personal devices or personal computer running specialized software. The data can be provided to computing device 50 over a wireless connection 44, using the internet (not depicted), or with a direct wired connection (not depicted). Computing device 50 includes a processor, input devices, visual display, and may include an output device such as a printer (not depicted). The specialized application may be provided which runs a database program to store and analyze data. The application or program may be run from computing device 50 hard drive, or from a server or other computing device operably connected over a network to the computer or mobile device. The database of data may be stored in memory, which may be local or may be stored in another device connected over a network.

In an embodiment, time domain reflectometer 12 is capable of operating for extended periods on a low power voltage source such as alkaline batteries. The low power consumption is achieved due to the low quiescent current requirements of the preferred devices for the voltage regulator, any memory devices, relay 48, and computing device 50. Computing device 50 will also support low power consumption by using a low power mode. The system and apparatus may also itself use a low power mode which includes turning off the oscillator driver, so the device is run on a low standby current.

Figure 3:
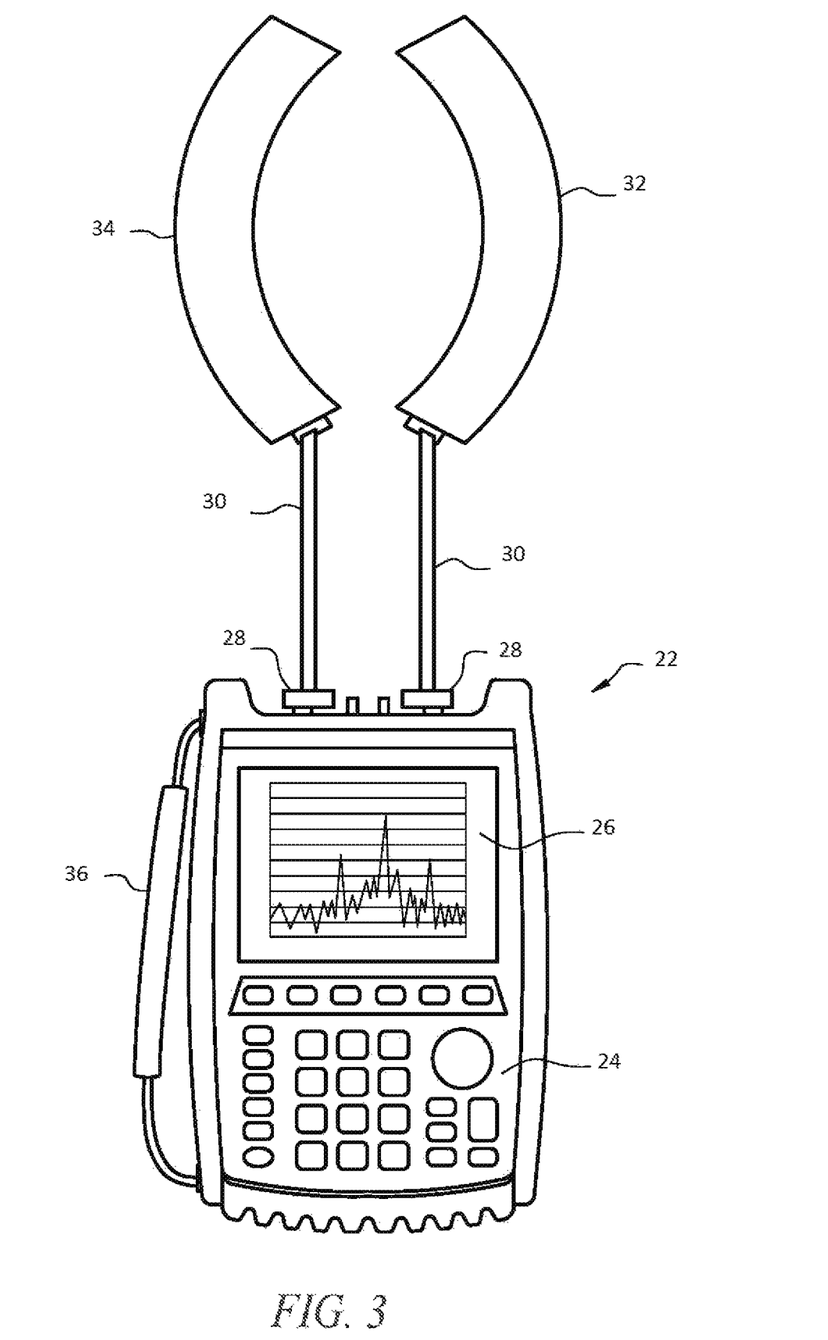
FIG. 3 depicts an alternate embodiment of the claimed subject matter.

In a second embodiment, depicted in FIG. 3, apparatus for detecting pests involves a portable dielectric detector 22, instead of apparatus 10, time domain reflectometer 12, outgoing transmission line 14, incoming transmission line 15, and capacitance sensor 20, used in the embodiment depicted in FIG. 1. Dielectric detector 22 includes a microwave spectrum analyzer 26, used to display dielectric data. The portable dielectric detector 22 further includes a TSA array transmitter 32 and a TSA array receiver 34, which gather dielectric data that is displayed on microwave spectrum analyzer 26. The TSA array transmitter 32 and TSA array receiver 34 are coupled to adaptor 28 via microwave transmission cables 30. The portable dielectric detector 22 can be held by a user utilizing strap 36. The portable dielectric detector 22 can monitor signals from 50 MHz to 40 GHz. The microwave spectrum analyzer 26 can be tuned with controls 24 to the desired detection range within the 50 MHz to 40 GHz range. The TSA array transmitter 32 transmits microwaves through the tree 40 (as depicted in FIG. 4 discussed below) to TSA array receiver 34, this dielectric data is then transmitted to the portable dielectric detector 22. Portable dielectric detector 22 monitors target region with appropriate placement of the TSA array transmitter 32 and TSA array receiver 34 to analyze the returning signal and the presence of pests inside living systems, such as a tree 40 (as depicted in FIG. 4 discussed below). Portable dielectric detector 22 may also monitor target region in other living systems, such as shrubs, vines, grasses, or any other living system that may contain pests.

When the pests damage the structure of the tree 40, the dielectric constant of the damaged area changes. This change in dielectric constant in the damaged area results in a higher dielectric constant than the dielectric constant of an undamaged area. In some circumstances, the damaged area may result in a lower dielectric constant than an undamaged area of interest, for example, in a tree 40. The apparatus indicates changes to tree 40, from a known baseline which can provide data on possible pest activity in the environment, such as a tree 40. Whether the damaged area in the living system from pest activity results in a higher dielectric constant than undamaged areas or lower dielectric constant than undamaged areas depends on the living system under investigation, the specific time in the life cycle of the pest, and the type of pest causing the damage. For example, pest activity may lead to decreased water and moisture inside the target region than the undamaged regions by hollowing out portions of tree 40, this would lead to a lower dielectric constant than an undamaged area.

In an embodiment depicted in FIG. 4, the TSA array transmitter 32 and the TSA array receiver 34 are arranged opposite each other around the trunk of tree 40 so that dielectric data from the area between the transmitter and receiver is collected. In some embodiments, multiple transmitters 32 are arranged opposite multiple receivers 34 to cover additional area within tree 40. The portable dielectric detector 22 is also configured to receive manual input regarding, for example, baseline values of undamaged areas of the tree 40. The portable dielectric detector 22 is operatively linked to a receiver (not depicted). The pest reporting system can provide degree of infestation, location, duration, and quality of pest activity. The location and duration of readings may be entered manually by the user, to indicate in space and time where the readings were taken. In some embodiments, computing device 50 will time stamp and provide GPS coordinates to each set of data from the portable dielectric detector 22.

As discussed above, the degree of pest activity and quality of pest activity is determined by comparing capacitance or dielectric data gathered in the area of interest to baseline values of the environment or undamaged areas of the tree 40. The computing device 50 can be any one of a mobile device, a personal digital assistant, a computer, or any other device having a processor and a non-transitory storage medium. This is accomplished by performing a canonical discriminant analysis of the frequency sweep curves obtained either by the time domain reflectometry or by the transmission spectrometry. The identified discriminants varying from the baseline are correlated to the presence (and population) of a corresponding pest.

The pest monitoring system and apparatus may be employed as a standalone device, such as a portable dielectric detector 22 or in connection with multiple portable dielectric detector devices (not depicted) as part of a report generation system, and also can include the ability to provide additional dielectric data on the target region, the pests, and the comparison of the resulting dielectric reading with either a baseline reading or a standardized reading. As used in the present application, target region is a region of interest under analysis. When analyzing a tree 40, for example, the target region can include specific areas of a tree 40 such as a few feet of the trunk, the entire trunk of a tree, or an entire tree.

The advantages set forth above, and those made apparent from the foregoing description, are efficiently attained. While the disclosure is susceptible to various modifications and implementation in alternative forms, specific embodiments have been shown by way of non-limiting example in the drawings and have been described in detail herein. Since certain changes may be made in the above construction without departing from the scope of the instant application, it is intended that all matters contained in the foregoing description or shown in the accompanying drawings shall be interpreted as illustrative and not in a limiting sense.

The disclosure is not intended to be limited to the particular forms disclosed. Rather, the disclosure is to cover all modifications, equivalents, and alternatives falling within the scope of the disclosure as defined by the following appended claims and their legal equivalents.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art, and having the benefit of this disclosure, that changes may be made to the details of the above-described embodiments without departing from the underlying principles of the disclosure herein.

It is also to be understood that the following claims are intended to cover all of the generic and specific features of the invention herein described, and all statements of the scope of the invention that, as a matter of language, might be said to fall therebetween.

What is claimed is:

1. An apparatus for detecting pest activity in a living system, comprising:
   a capacitive sensor;
   an inbound transmission line and an outbound transmission line coupled to the capacitive sensor;
   a capacitive sensing time domain reflectometry (TDR) device, wherein the TDR device is both a source and a detector of signals transmitted to and from a region of detection or an area of interest; and
   a probe enclosing the inbound and outbound transmission lines, the probe having a proximal end and a distal end, the distal end of the probe operably linked to the capacitive sensor, wherein the TDR device transmits a signal as an incident waveform via an outbound transmission line to the capacitive sensor, whereby the signal is reflected from the capacitive sensor via the inbound transmission line back to the TDR device;
   wherein the TDR device determines a measured capacitance value of the object based on the reflected signal, whereby the measured capacitance value is compared against a predefined baseline capacitance value of an uninfected region of the object, whereby a deviation of the measured capacitance value from the predefined baseline capacitance value indicates presence of the pest activity.

2. The apparatus of claim 1, wherein the probe is configured to penetrate a living tree.

3. The apparatus of claim 1, wherein the TDR device is operably linked to a computing device.

4. The system of claim 3, wherein the computing device is configured to display the results from the capacitance electrode sensors.

5. The apparatus of claim 1, wherein the pest is selected from the group consisting of a termite and an emerald ash borer.

6. The apparatus of claim 2, wherein the living tree is selected from a group consisting of a pine, an ash, and an oak tree.

7. The apparatus of claim 1, wherein the apparatus is wirelessly linked to a computing device, thereby enabling the TDR to wirelessly transmit the measured capacitance value to the computing device.

8. A system for detecting pest activity within a living system, the system comprising:
- a portable dielectric detector having a microwave spectrum analyzer;
- a microwave TSA array transmitter and TSA array receiver linked via microwave transmission cables to the portable dielectric detector, wherein the TSA array transmitter transmits a microwave signal and the TSA array receiver receives the microwave signal, wherein the TSA array transmitter and TSA array receiver are attached to the living system;
- wherein the received microwave signal provides a dielectric value measured within the object, the measured dielectric value being compared against a predefined baseline dielectric value of an unaffected region of the living system, whereby a deviation of the measured dielectric value from the baseline dielectric value indicates presence of the pest activity within the living system.

9. The system of claim 8, wherein the living system is a living tree.

10. The system of claim 8, wherein the microwave spectrum analyzer displays changes in the measured dielectric value.

11. The system of claim 10, wherein pest activity results in an increase in the deviation of the measured dielectric value from with respect to the predefined baseline dielectric value.

12. The system of claim 8, wherein the pest is selected from a group consisting of a termite and an emerald ash borer.

13. The system of claim 9, wherein the living tree is selected from a group consisting of a pine, an ash, and an oak tree.

14. The system of claim 8, wherein the microwave spectrum analyzer is wirelessly linked to a computing device, thereby enabling the microwave spectrum analyzer to wirelessly transmit the measured dielectric value to the computing device.

15. A method of detecting pest activity within a living system, the method comprising:
- providing a time domain reflectometer at a proximal end of a transmission line and a capacitance sensor at a distal end of the transmission line;
- inserting the capacitance sensor into an interior of the living system;
- generating a signal from the time domain reflectometry source/detector;
- transmitting an incident waveform of the signal distally along the transmission line and through the capacitance sensor into the interior of the living system;
- receiving, by the capacitance sensor, the signal reflected from the interior of the living system;
- transmitting a reflected waveform of the signal proximally along the transmission line back to the time domain reflectometer; and
- comparing the reflected waveform against a predefined baseline value, wherein a deviation of the reflected waveform from a baseline value indicates presence of the pest activity.

\* \* \* \* \*